United States Patent
Altstein

(12) 
(10) Patent No.: US 6,358,927 B1
(45) Date of Patent: *Mar. 19, 2002

(54) PEPTIDE FRAGMENTS AND ANALOGS DERIVED FROM PBAN 1-33 NH$_2$ FOR CONTROLLING MOTHS

(75) Inventor: Miriam Altstein, Rehovot (IL)

(73) Assignee: State of Israel (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/727,488

(22) PCT Filed: Apr. 18, 1995

(86) PCT No.: PCT/EP95/01448

§ 371 Date: Dec. 18, 1996

§ 102(e) Date: Dec. 18, 1996

(87) PCT Pub. No.: WO95/29191

PCT Pub. Date: Nov. 2, 1995

(30) Foreign Application Priority Data

Apr. 24, 1994 (IL) .................................................. 109405

(51) Int. Cl.[7] .......................... A61K 38/08; C07K 7/06; A01N 25/00
(52) U.S. Cl. ......................... 514/15; 530/328; 530/858; 424/405; 424/198.1
(58) Field of Search ............................. 514/12, 15, 17; 424/405, 198.1; 530/324, 328, 329, 858

(56) References Cited

U.S. PATENT DOCUMENTS 4,423,037 A * 12/1983 Rosenblatt et al. ......... 424/177
5,032,576 A  7/1991 Raina et al. ................... 514/12
5,304,672 A * 4/1994 Labovitz ......................... 56/51

FOREIGN PATENT DOCUMENTS

JP         4208300          7/1992

OTHER PUBLICATIONS

Hruby VJ. Strategies in the development of peptide antagonists. Prog Brain Res 1992:92:215–24.*
Kempe et al. Seventh International Congress of Pesticide Chem. Pesticide Sci. 30, 436 Aug. 1991.*
Structure Activity Studies of PBAN of *Helicoverpa Zea* (Lepidoptera:Noctuidae), by A. K. Raina et al., *Insect Biochem. Molec. Biol.* vol. 22, No. 3, 1992, pp. 221–225.
N–Terminal Modified Analogs of C–Terminal Fragments of PBAN With Pheromonotropic Activity, by H. Kuniyoshi et al., *Insect Biochem. Molec. Biol.* vol. 22, No. 4, 1992, pp. 399–403.
Archives of Insect Biochemistry and Physiology, by R. J. Nachman et al., vol. 22, No. 1/2, 1993, pp. 181–197.
Riddiford et al, The Biological Bulletin, vol. 140, No. 1, pp. 1–7 (Feb. 1971).
Raina et al, Science, vol. 225, pp. 531–533 (Aug. 1984).
Altstein et al, Archieves of Insect Biochemistry and Physiology, 22:153–168 (1993).
Raina, Annu. Rev. Entomol., vol. 38, pp. 329–349 (1993).

* cited by examiner

*Primary Examiner*—David S. Romeo
(74) *Attorney, Agent, or Firm*—Birch, Stewart, Kolasch & Birch LLP

(57) ABSTRACT

Synthetic peptide fragments from pheromone biosynthesis activating neuropeptide PBAN (1-33)-NH$_2$ of *Helicoverpa zea* which have either pheromone biosynthesis stimulating or inhibiting activity.

4 Claims, 6 Drawing Sheets

US 6,358,927 B1

PEPTIDE FRAGMENTS AND ANALOGS DERIVED FROM PBAN 1-33 NH₂ FOR CONTROLLING MOTHS

FIELD OF THE INVENTION

This invention relates to peptide fragments and analogs derived from the amino acid sequence of PBAN 1-33 $NH_2$ (PBAN=pheromone biosynthesis activating neuropeptide) showing stimulatory and inhibitory biological activities at doses similar to those of PBAN 1-33 (10–100 pmol). These peptide fragments serve as a basis for the design of insecticides aimed at the disruption of pheromone production, melanization and other activities controlled by PBAN 1-33 $NH_2$ and derived fragments.

Said invention further relates to a method for controlling adult female moths and insects by applying the above mentioned peptide fragments or peptidomimetic compounds derived from their sequence to any agricultural produce to inhibit pheromone production.

BACKGROUND OF THE INVENTION

Neuropeptides play a key role in the regulation of a variety of physiological functions in insects. These endocrine cues are involved in embryonic and post-embryonic developmental processes (such as molting, diapause and metamorphosis), in homeostasis, osmoregulation, diuresis and digestion. Insect neuropeptides are also known to control essential behavioral patterns such as migration, mating and oviposition. In recent years, the development of improved chemical, biochemical and molecular techniques has facilitated the identification of insect neuropeptides and resulted in the isolation and characterization of over fifty compounds.

Due to their substantial involvement in a variety of physiological processes, studies of insect neuropeptides introduce a new insight into basic life processes which may serve as an excellent basis for comparative neuroendocrine studies aimed to understand the evolutionary history of basic biological events. In addition, insect neuropeptides provide new targets for pest control which are based on the interference with their activity. This strategy requires a better understanding of the cascade of events common to the neuroendocrine regulation, namely: biosynthesis, release, transport, binding and activation of the target organ. So far, our understanding of these events for most insect neuropeptides is very limited. The present invention concentrates centrates on some of these aspects comprising the activity of peptide fragments derived from PBAN, which is known to regulate sex-pheromone biosynthesis and melanization in moths.

Sexual communication between male and female moths is regulated mainly by sex pheromones. Sex pheromones are synthesized and secreted by the female moth from the pheromone gland which is located at the intersegmental membrane between the eighth and the ninth abdominal segments. The inability of the female moth to produce sex pheromones results in a marked decrease in mating and thus, a significant reduction in the size of the population. Due to their important role in mating, sex pheromones have been studied intensively. In the past 30 years more than two hundred sex pheromones were isolated and identified. These studies revealed that moths sex pheromones consist of blends of C10–C18 aliphatic compounds, most of which have one or more double bonds. The diversity between pheromones of different species is indicated by differences in the chain length, the position and configuration of the olefinic bonds, and by the chemical nature of the functional group. Most pheromones are aldehydes, alcohols or acetates. Some, however, may-appear as epoxides, ketones and hydrocarbons.

While the structural and behavioral aspects of sex pheromones in Lepidopterans have been studied intensively, the endogenous mechanisms that control sex pheromone biosynthesis are not fully understood. The possible involvement of a cerebral factor in this process was first proposed in 1971 by Riddiford and Williams (Biol. Bull. 140, 1–7). Direct evidence of the involvement of a neuroendocrine factor in the regulation of sex pheromone biosynthesis was demonstrated for the first time only thirteen years later by Raina and Klun, (Science 225, 531–533, 1984) in *Helico-verpa zea*. The neuroendocrine factor was termed pheromone biosynthesis activating neuropeptide (PBAN), and since 1984 its presence has been demonstrated in a variety of moth species. Since its discovery PBAN was characterized as a linear C-terminally amidated peptide containing 33 amino acids. The primary structure of PBAN has been fully identified in two moth species: *Helicoverpa zea* and *Bombyx mori* and its gene and cDNA have been cloned from the same two insects. PBAN is synthesized in the subesophageal ganglion and is transported to its target organ via the hemolymph and/or the ventral nerve cord. It is present in both male and female moth and its biological activity is mediated by cAMP and depends on the presence of $Ca^{++}$ ions. In addition to its pheromonotropic activity PBAN and fragments derived from its sequence also control cuticular melanization, muscle contraction and diatause (for review see Altstein et al, Arch. Insect. Biochem. and Physiol. 22, 153–168, 1993; Raina, Ann. Rev. Entomol. 38, 329–349, 1993).

Despite the fact that PBAN has been studied for almost ten years, the understanding of its activity is quite limited, and most of the studies concentrate on: A) its release and transport; B) identification of its target organ; and C) its cellular activity. Among the various steps associated with the activity of the neuropeptide most effective and specific target for inhibition is the binding site of PBAN. Such an inhibition can be acquired by antagonists, which are selective inhibitors capable of locking the receptor site of the neuropeptide, and thus, preventing from the endogenous peptide to bind to the receptor and exert its biological activity. PBAN antagonists are, therefore, specific inhibitors for the production of sex pheromones. Since neuropeptides are chemically unstable and readily attacked by enzymes the strategy for the development of the antagonistic compounds is based on creating peptide-derived compounds (peptidomimetic compounds) which are biologically stable, and exhibit extended antagonistic activity. This strategy is novel and was never applied before for insect control.

In order to design peptidomimetic antagonists the structure-activity relationship of PBAN has to be revealed, and the active and inactive sequences in the molecule have to be identified. The main achievements of the study are:

A) The identification of the shortest fragment (six amino acids) derived from the sequence of Hez-PBAN that evokes pheromonotropic activity in the moth *Heliothis peltigera* at doses similar to those of Hez-PBAN 1-33 $NH_2$ (synthetic PBAN, based on the sequence of the peptide isolated from *Helicoveria zea*).

B) The identification of a 10 amino acid fragment derived from the original sequence of PBAN which exhibits partial antagonistic activity.

The finding that these two fragments are short peptides introduces the following advantages:

A) The number of possible derivatives that has to be screened in the course of the search for a potent antagonist is several orders of magnitude lower than the number that has to be screened in the case of a large peptide. This may shorten significantly the first stage of the search for a lead antagonist.

B) The production of a 10 or less amino acid pedtide is based on available equipment and technologies and is most efficient.

C) This finding is in line with the common practice in the insecticide industry that insecticides, particularly those applied to adult insects, should be of low molecular weight, in order to penetrate the insect's cuticle.

These achievements enable the application of strategies similar to those for rational drug design to search for peptidomimetic PBAN antagonists.

Two patent applications have been filed so far with respect to PBAN:

A) A Japanese patent application No. 4-208300 (Suzuki et. al) which relates to the full 33 amino acid sequence peptide isolated from silkworms, and also to some of its fragments. These peptides, according to this patent application are activating the pheromone bio-synthesis in silkworms. The Japanese application does not relate to the use of these peptides as a source and a basis for the design of lead compounds and potential agonists and antagonists for PRAN. Moreover, the experimental biological conditions and the concentrations in which the activity is observed in the J.P. patent application are totally different from the present invention. The concentrations of the peptides for obtaining activity are 100 times higher in the J.P. patent application than in the present application B) A U.S. Pat. No. 5,032,576 (Raina et al.,) which relates to the isolation, characterization and synthesis of PBAN from *Helicoverpa zea*. The patent also refers to the use of the full length PBAN 1-33 $NH_2$ and some of its analogs (all of which are 33 amino acid long) as methods for controlling female moths or larvae. Said US patent does not relate to the biological activity of shorter fragments derived from the sequence of Hez-PBAN or their use as means for insect control.

SUMMARY OF THE INVENTION

The present invention provides peptide fragments and analogs derived from the amino acid sequence of Hez-PBAN 1-33 $NH_2$ showing stimulatory (agonistic) and inhibitory (antagonistic) biological activities at doses similar to those of PBAN 1-33 (10–100 pmol) for use as a basis for the design of insecticides aimed at the disruption of pheromone production, melanization and other activities controlled by PBAN 1-33 $NH_2$ and derived fragments.

Said invention further provides a method for controlling adult female Heliothis, moths and insects by applying the above mentioned peptide fragments or peptidomimetic compounds derived from their sequence to any agricultural produce to inhibit pheromone production. More specifically, the preferred peptide fragments according to the invention are as follows:

a) R-Tyr-Phe-Ser-Pro-Arg-Leu-$NH_2$ (SEQ ID NO: 2) wherein R represents H, Ac, Bz, Bzl, Et, showing stimulatory activity at doses of 10 pmol in a pheromonotropic bioassay at times ranging from 30–60 min.

b) H-Pro-Ala-Asp-Gln-Glu-Met-Tyr-Arg-Gln-Asp-COOH (SEQ ID NO: 3), showing inhibitory activity in the presence of PBAN 1-33 $NH_2$.

c) H-Pro-Ala-Asp-Gln-Glu-Met-Tyr-Arg-Gln-Asp-COOH (SEQ ID NO:3) that shows inhibitory activity in the presence of PBAN 1-33 $NH_2$ and or derived peptides resulting in the inhibition of pheromone production in female moths.

d) H-Pro-Ala-Asp-Gln-Glu-Met-Tyr-Arg-Gln-Asp-COOH (SEQ ID NO:3) that shows inhibitory activity in the presence of PBAN 1-33 $NH_2$ and or derived peptides resulting in the inhibition of melanin production in moth larvae.

DETAILED DESCRIPTION OF THE INVENTION

Figure 1:
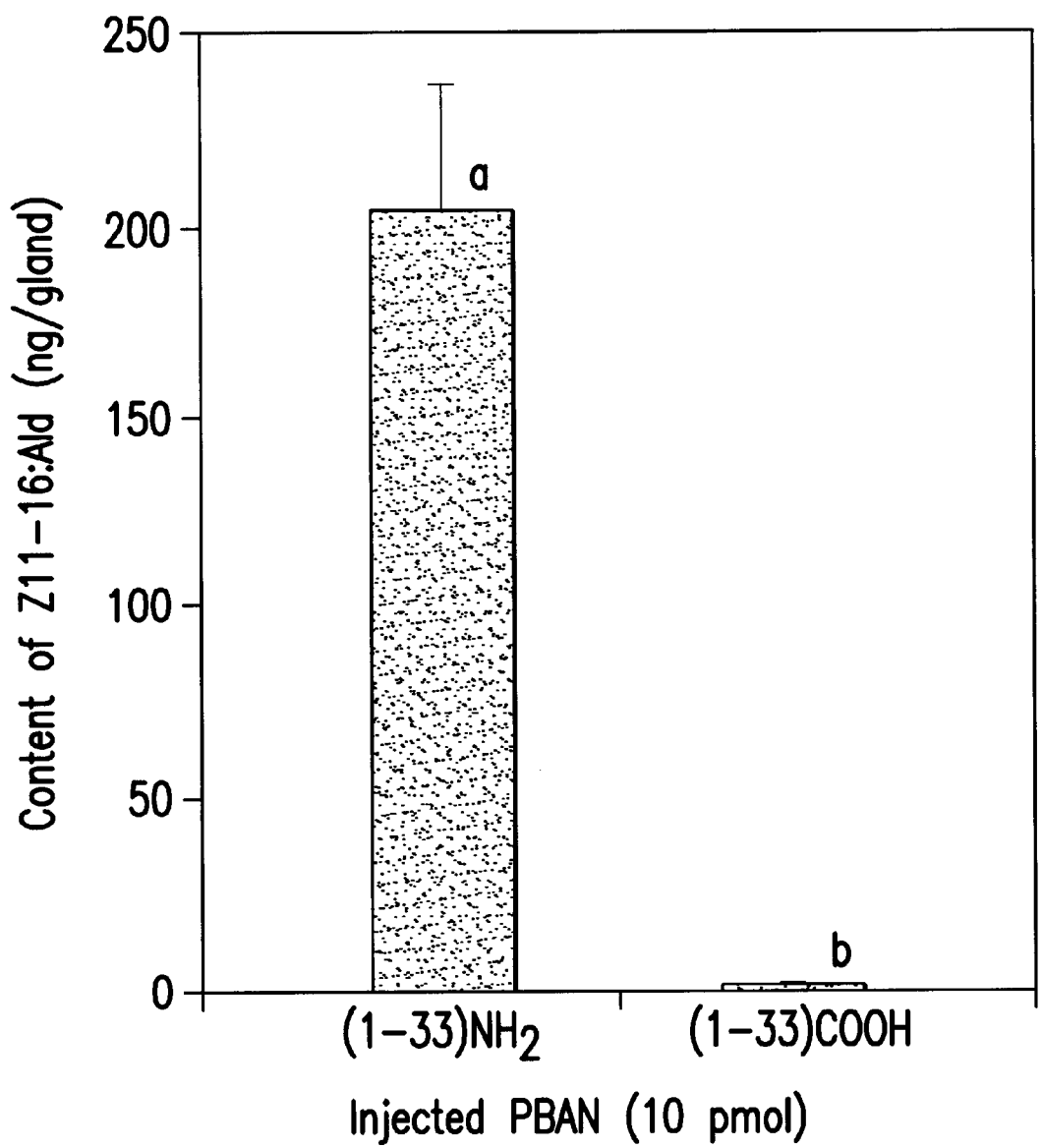
FIG. 1 shows the pheromonotropic activity of amidated and free acid PBAN 1-33. Pheromone content is represented by the amount of the major pheromone component Z11-16:Ald. Values with the same letter do not differ significantly.

Structure activity studies were performed by an examination of the pheromonotropic activity of synthetic Hez-PAN (PBAN 1-33 $NH_2$) and ten shorter fragments derived from its N- and C-terminal regions. Activity was tested on *Heliothis peltigera* using a bioassay as described by Gazit et al; (Insect Biochem., 20, 853–858, 1990). These structures are as follows:

Amidated Peptides

H-Leu$^1$-Ser-Asp-Asp-Met-Pro-Ala-Thr-Pro-Ala$^{10}$-Asp-Gln-Glu-Met-Tyr-Arg-Gln-Asp-Pro-Glu$^{20}$-Gln-Ile-Asp-Ser-Arg-Thr-Lys-Tyr-Phe-Ser$^{30}$-Pro-Arg-Leu$^{33}$-$NH_2$= PBAN (1-33) $NH_2$ (SEQ ID NO: 1)

H-Pro-Ala$^{10}$-Asp-Gln-Glu-Met-Tyr-Arg-Gln-Asp-Pro-Glu$^{20}$-Gln-Ile-Asp-Ser-Arg-Thr-Lys-Tyr-Phe-Ser$^{30}$-Pro-Arg-Leu$^{33}$-$NH_2$ (SEQ ID NO: 5)=PBAN (9-33) $NH_2$

H-Glu-Met-Tyr-Arg-Gln-Asp-Pro-Glu$^{20}$-Gln-Ile-Asp-Ser-Arg-Thr-Lys-Tyr-Phe-Ser$^{30}$-Pro-Arg-Leu$^{33}$-$NH_2$=PBAN (13-33) $NH_2$ (SEQ ID NO:6)

H-Gln-Asp-Pro-Glu$^{20}$-Gln-Ile-Asp-Ser-Arg-Thr-Lys-Tyr-Phe-Ser$^{30}$-Pro-Arg-Leu$^{33}$-NH$_2$=PBAN (17-33) NH$_2$ (SEQ ID NO: 7)

H-Pro-Glu$^{20}$-Gln-Ile-Asp-Ser-Arg-Thr-Lys-Tyr-Phe-Ser$^{30}$-Pro-Arg-Leu$^{33}$-NH$_2$=PBAN (19-33) NH$_2$ SEQ ID NO: 7

H-Thr-Lys-Tyr-Phe-Ser$^{30}$-Pro-Arg-Leu$^{33}$-NH$_2$ (SEQ ID NO: 8)=PBAN (26-33) NH$_2$

H-Tyr-Phe-Ser$^{30}$-Pro-Arg-Leu$^{33}$-NH$_2$ (SEQ ID NO: 9)=PBAN (28-33) NH$_2$

Free Acid Peptides

H-Leu$^1$-Ser-Asp-Asp-Met-Pro-Ala-Thr-Pro-Ala$^{10}$-Asp-Gln-Glu-Met-Tyr-Arg-Gln-Asp-Pro-Glu$^{20}$-Gln-Ile-Asp-Ser-Arg-Thr-Lys-Tyr-Phe-Ser$^{30}$-Pro-Arg-Leu$^{33}$-COOH (SEQ ID NO: 1)=PBAN (1-33) COOH

H-Pro-Ala$^{10}$-Asp-Gln-Glu-Met-Tyr-Arg-Gln-Asp-Pro-Glu$^{20}$-Gln-Ile-Asp-Ser-Arg-Thr-Lys-Tyr-Phe-Ser$^{30}$-Pro-Arg-Leu$^{23}$-COOH (SEQ ID NO:4)=PBAN (9-33) COOH

H-Pro-Glu$^{20}$-Gln-Ile-Asp-Ser-Arg-Thr-Lys-Tyr-Phe-Ser$^{30}$-Pro-Arg-Leu$^{33}$-COOH=PBAN (19-33) COOH (SEQ ID NO: 7)

H-Pro-Ala$^{10}$-Asp-Gln-Glu-Met-Tyr-Arg-Gln-Asp$^{18}$-COOH (SEQ ID NO: 3)=PBAN (9-18COOH

The role of the N-terminus on the onset of the biological activity was examined using a series of peptides lacking 8, 12, 16, and 18 amino acids from their N-terminus [PBAN (9-33) NH$_2$, PBAN (13-33) NH$_2$, PBAN (17-33) NH$_2$ and PBAN (19-33) NH$_2$], respectively. Fragments were examined at 1 pmol (a dose where the full length molecule exhibits maximal activity). Pheromone content was examined two hours post-injection. The results revealed that PEAN (9-33) NH$_2$ is active as PBAN (1-33) NH$_2$ (Table 1). The other fragments, however, were inactive at this dose except for PBAN (19-33) NH$_2$ which exhibited a low activity (Table 1). Based on these data it was concluded that the first eight N-terminal amino acids are not essential for the onset of the pheromonotropic activity, whereas the sequence between amino acids 9–12 is essential. Injection of a higher dose (10 pmol) of the above fragments revealed that peptides lacking even 18 amino acids from their N-terminus are as active as the full length PBAN (Table 1). These results hinted at the possibility that the active site of the neuropeptide is not contained within the first 18 N-terminal amino acids, and raised the possibility that the active site is contained within the C-terminal region. The N-terminal region may provide stability against proteolytic degradation or alternatively may play a secondary structural role.

TABLE 1

Pheromonotropic activity of PBAN (1-33) NH$_2$ and derived peptides.
Pheromone content
Z11-16:Ald ng/gland ± SE

| Injected peptide | Dose of 1 pmol | Dose of 10 pmol |
| --- | --- | --- |
| PBAN (1-33) NH$_2$ | 200.7 ± 40.7 a | 225.2 ± 51.4 a' |
| PBAN (9-33) NH$_2$ | 143.7 ± 29.6 a | 168.0 ± 9.2 a' |
| PBAN (13-33) NH$_2$ | 4.1 ± 3.0 d | 180.2 ± 47.3 a' |
| PBAN (17-33) NH$_2$ | 24.1 ± 5.7 c | 196.9 ± 40.7 a' |
| PBAN (19-33) NH$_2$ | 52.7 ± 21.0 b | 133.8 ± 15.7 b' |
| PBAN (26-33) NH$_2$ | 8.9 ± 3.5 d | 12.2 ± 3.1 c' |
| PBAN (28-33) NH$_2$ | 5.6 ± 1.7 d | 12.7 ± 4.9 c' |

Pheromonotropic activity was determined by injecting the peptides, dissolved in buffer phosphate to 3.5–4.5 days old females during daylight for two hours. Pheromone content is represented by the amount of the major pheromone component Z11-16:Ald. Values with the same letter do not differ significantly.

Figure 2A:
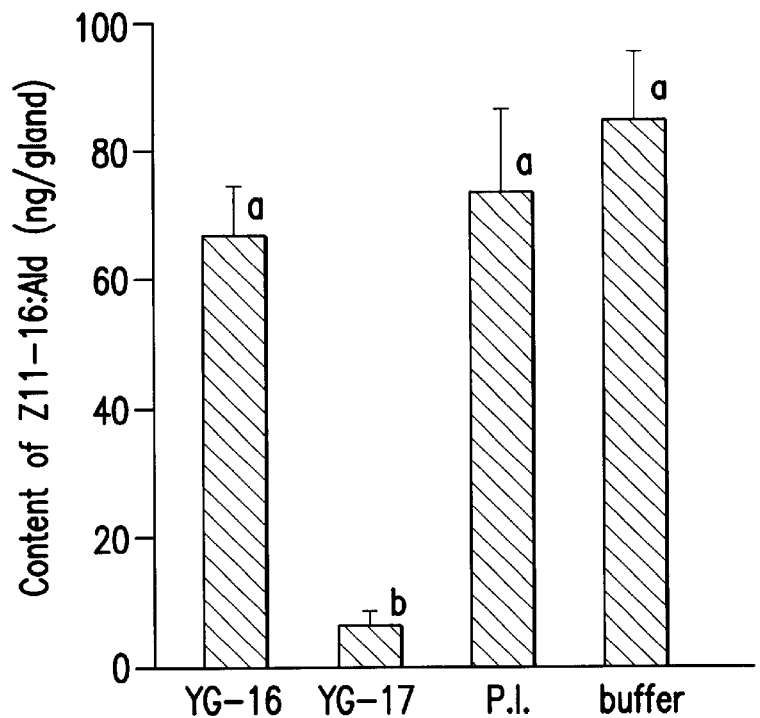
FIG. 2 shows sex pheromone synthesis in the presence and absence of N- and C-terminally directed antisera (YG-16 and YG-17, respectively). Sex pheromone biosynthesis was induced either by exogenously administered PBAN (FIG. 2A) or endogenous PBAN (FIG. 2B). P.I.—pre-immune serum. Pheromone content is represented by the amount of the major pheromone component Z11-16:Ald. Values with the same letter do not differ significantly.
Figure 2B:
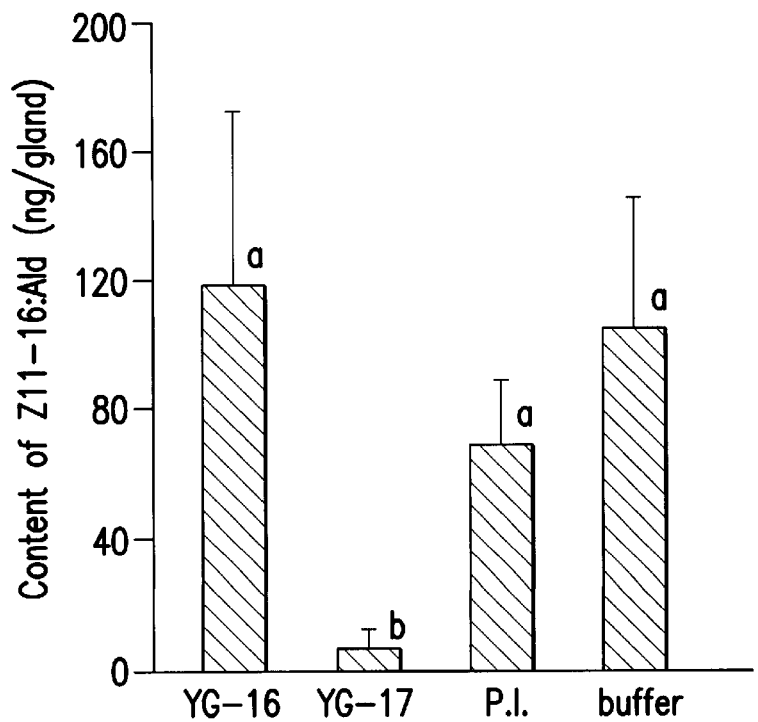
Figure 3:
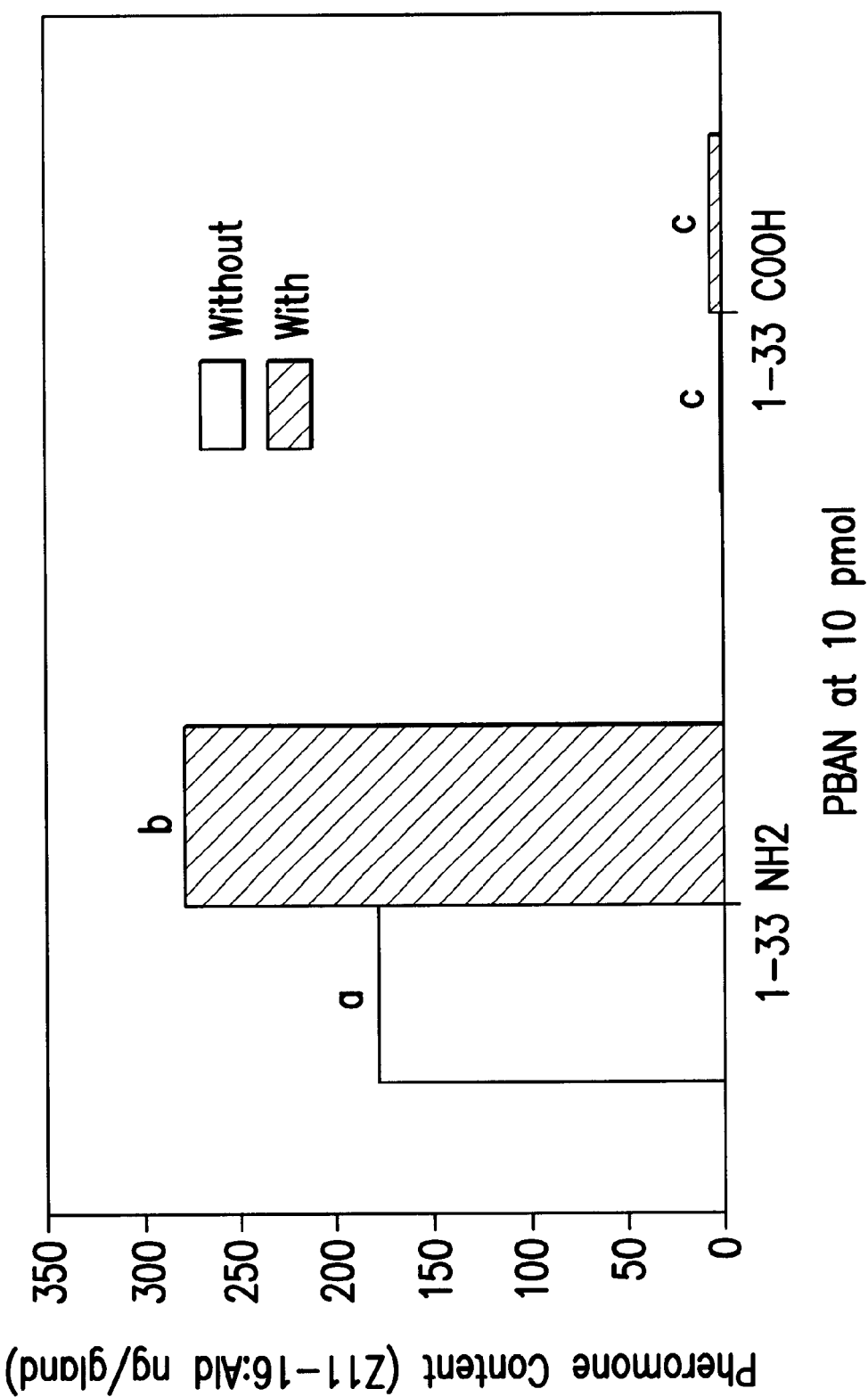
FIG. 3 shows the biological acitivity of amidated and free acid PBAN 1-33 in the presence of protease inhibitors. Pheromone content is represented by the amount of major pheromone component Z11-16:Ald. Values with the same letter do not differ significantly.

The role of the C-terminus in the biological activity was examined using a free acid molecule of PBAN [PBAN (1-33) COOH]. This molecule was completely inactive even at 10 pmol (FIG. 1), indicating the importance of the C-terminally amide. The importance of this part of the molecule was also confirmed with a C-terminally directed antiserum YG-17(3), which blocked the activity of exogenously administered and endogenous PBAN (FIG. 2). In order to test wether the C-terminally amide of PBAN has a protective effect against proteolysis or is a conformational requirement for the PBAN receptor, the biological activity of PBAN (1-33)COOH was examined in the presence of a mixture of carboxypeptidase inhibitors (aprotinin and PMSF), and other protease inhibitors (TLCK, bacitracin). The addition of protease inhibitors did not enhance the biological activity of the free acid PBAN 1-33 COOH indicating that the C-terminally amide is a conformational requirement for receptor activation (FIG. 3) Analysis of the same mixture of inhibitors on the activity of the PBAN 1-33 NH$_2$ resulted in a significant stimulation in its activity, indicating the effectiveness of the treatment (FIG. 3).

Figure 4:
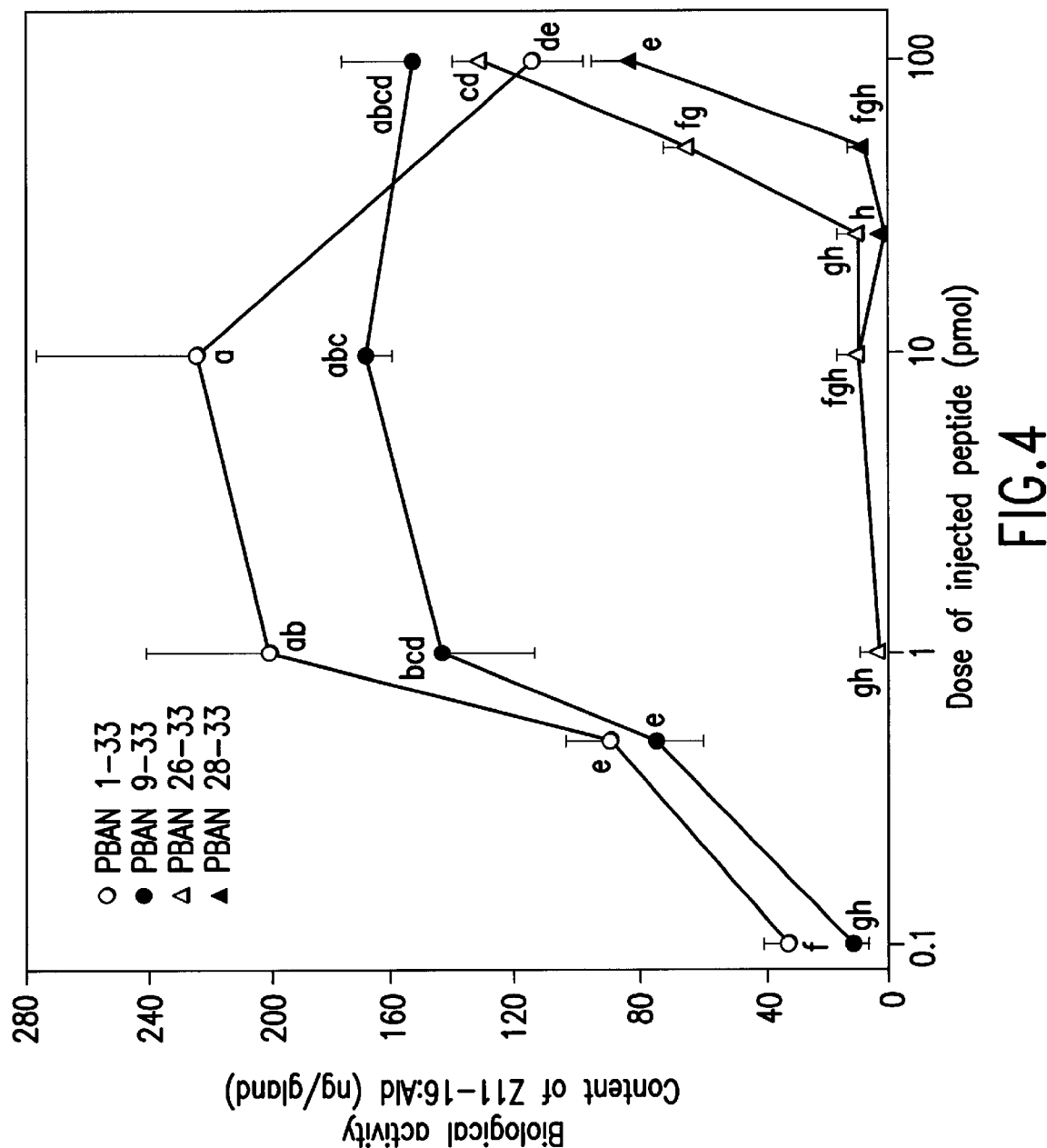
FIG. 4 shows the dose response curve of pheromonotropic activity evoked by PBAN 1-33 $NH_2$ and derived fragments. Pheromone content is represented by the amount of the major pheromone component Z11-16:Ald. Values with the same letter do not differ significantly.
Figure 5:
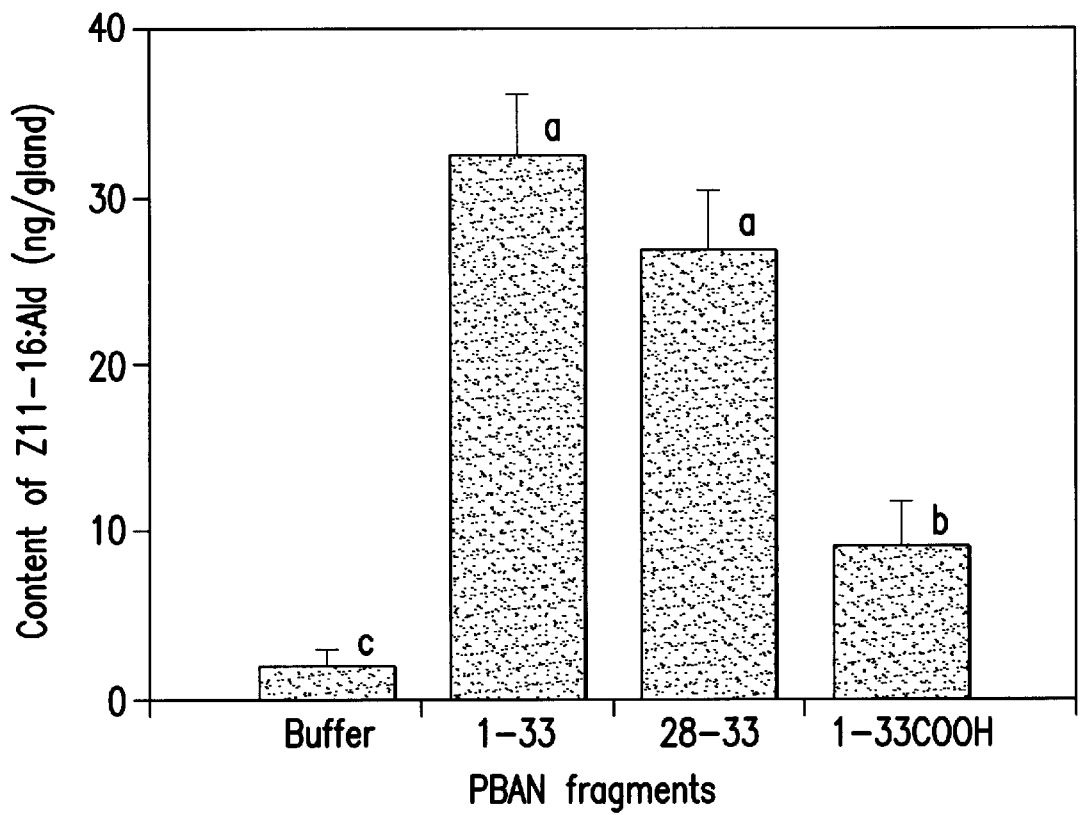
FIG. 5 shows pheromonotropic activity of PBAN 28-33 tested 15 min post injection. Pheromone content is represented by the amount of the major pheromone component Z11-16Ald. Values with the same letter do not differ significantly.

Further examination of the role of the C-terminal region in pheromonotropic activity involved analysis of two C-terminally derived fragments: PBAN (26-33) NH$_2$ and PBAN (28-33) NH$_2$. Preliminary analysis of the pheromonotropic activity of these peptides at concentrations ranging from 1–100 pmol revealed that they are active only at high doses (100 pmol) when tested 2 hours post injection (FIG. 4). However, analysis of the pheromonotropic activity of PBAN (28-33) NH$_2$ shortly after injection (15–30 min) revealed that the activity does not differ significantly from that of the full length PBAN (1-33) NH$_2$ (FIG. 5). Based on these results it was concluded that the hexapeptide contains the essential sequences required for the onset of the pheromonotropic activity and that within that sequence the C-terminally amide has a most important structural role. Thus, the hexapeptide can be useful as an excellent basis for the design of an antagonist lead compound for PBAN.

Examination of additional C-terminally free acid fragments derived from the sequence of PBAN (PBAN 9-33 COOH, PBAN 19-33 COOH and PBAN 9-18 COOH) revealed that these peptides lack any biological activity when injected at a dose of 10 pmol in the presence of protease inhibitors for 2 hours (Table 2).

TABLE 2

Pheromonotropic activity of C-terminally free acid peptides.

| Injected peptide (10 pmol) | Pheromone content Z11-16:Ald(ng/gland) ± SE |
| --- | --- |
| PBAN (1-33) COOH | 1.4 ± 0.76 |
| PBAN (9-33) COOH | <1 |
| PBAN (19-33) COOH | <1 |
| PBAN (9-18) COOH | <1 |

Figure 6:
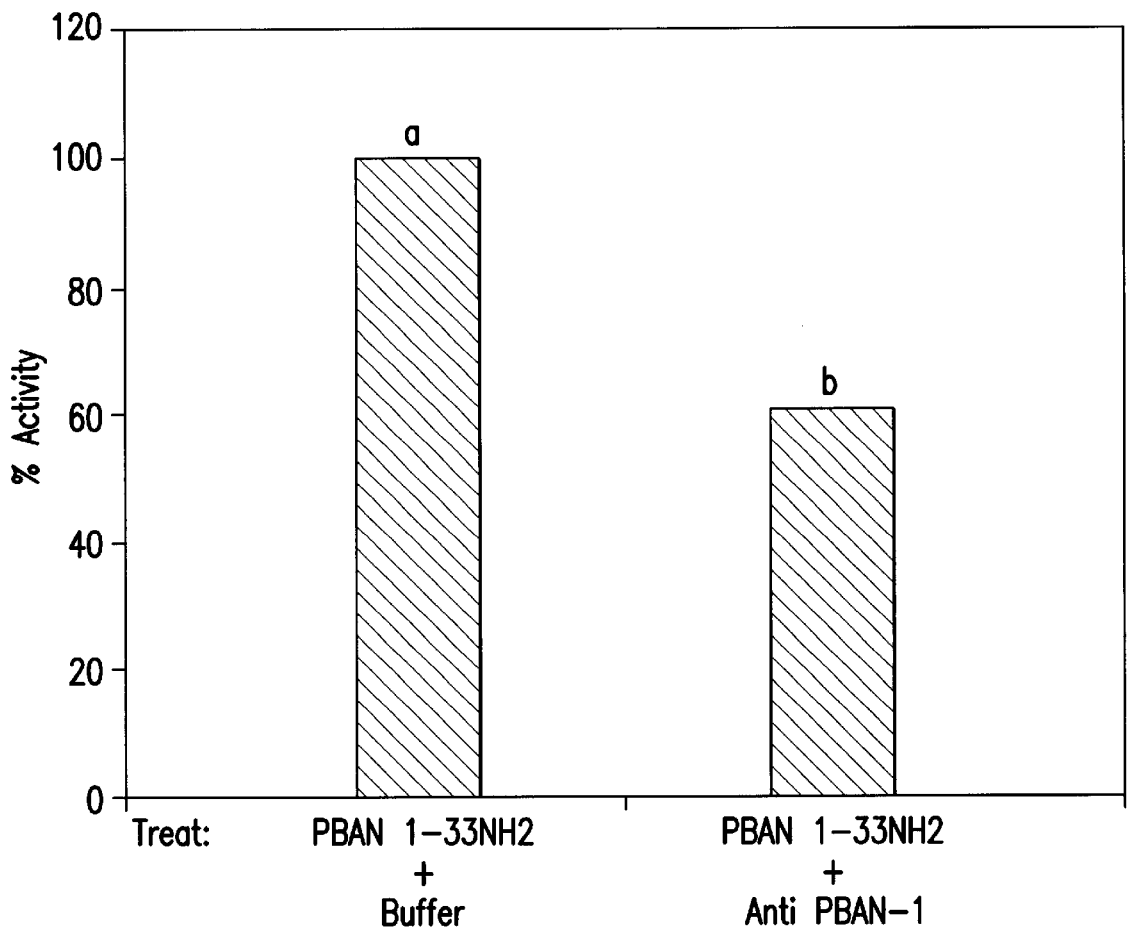
FIG. 6 shows the inhibitory effect of PBAN 9-33 on sex pheromone production evoked by PBAN 1-33 $NH_2$. PBAN 1-33 $NH_2$ was injected at a dose of 0.5 pmol and PBAN 9-33 COOH at a dose of 100 pmol. Anti PBAN-1 =PBAN 9-18 COOH. Values with different letters differ significantly.

Since inactive peptides derived from the sequence of a biologically active molecule often exhibit inhibitory activities, we have examined their effect on the pheromonotropic activity evoked by PBAN (1-33) NH$_2$. PBAN (1-33) COOH, PBAN (9-33) COOH and PBAN (19-33) COOH did not show any inhibitory activity when injected together with 1 pmol PBAN (1-33) NH$_2$. PBAN (9-18) COOH blocked the activity of the full length PBAN by 35% (Table 3). Injection of 0.5 pmol PBAN (1-33) NH$_2$ together with 100 pmol of PBAN (9-18) COOH resulted in a 40% inhibition of the pheromonotropic activity (FIG. 6). On the basis of these data we have concluded that PBAN (9-18) COOH is a competitive inhibitor for PRAN and serves as a partial antagonist for its activity. This sequence will serve as a basis for the design of additional antagonists which will fully inhibit the pheromonotropic activity of PBAN.

TABLE 3

Pheromonotropic activity of PBAN (1-33) $NH_2$ in the presence of free acid PBAN derived fragments.

| Injected peptide | Pheromone content Z11-16:Ald(ng/gland) ± SE | Inhibition (% of cont) |
|---|---|---|
| PBAN(1-33)$NH_2$ (control) | 165.0 ± 21.0 | — |
| PBAN(1-33)$NH_2$ + PBAN(1-33)COOH | 170.2 ± 24.2 | 0 |
| PBAN(1-33)$NH_2$ + PBAN(9-33)COOH | 154.7 ± 22.2 | 7 |
| PBAN(1-33)$NH_2$ + PBAN(19-33)COOH | 120.4 ± 29.2 | 27 |
| PBAN(1-33)$NH_2$ + PBAN(9-18)COOH | 108.1 ± 18.0 | 35 |

PBAN (1-33) $NH_2$ was injected at 1 pmol and the C-terminally free acid fragments at 10 pmol.

Structure activity studies were also performed with respect to the melanotropic activity of synthetic Hez-PBAN. All the fragments that were tested for their pheromonotropic activity were also tested for their melanotropic activity. Studies were performed on *Spodoptera littoralis* larvae using a quantitative bioassay (Altstein et al., Peptides, submitted, 1994) which examines the ability of PBAN fragments to induce cuticular melanization in ligated larvae. Ligated larvae produce smaller amounts of melanin compared to untreated larvae (Table 4) as a result of a reduction in their endogenous PBAN. Under the tested conditions ligation caused a significant, but not complete, reduction in cuticular melanization. This incomplete reduction may result from the presence of PBAN in ganglia which were not affected by the ligation or from the presence of another hormone or neuropeptide that affects this process. Injection of PBAN (1-33) $NH_2$ resulted in a significant increase in cuticular melanization, whereas injection of PBAN (9-18) COOH resulted in a significant decrease in cuticular melanization beyond the level obtained as a result of ligation or buffer injection (Table 4). These data indicate that PBAN (9-18) COOH antagonizes the activity of the endogenous PBAN which is still present in the larvae despite ligation. This sequence will serve as a basis for the design of additional antagonists which will fully inhibit the melanotropic activity of PBAN.

TABLE 4

Melanotropic activity of amidated and free acid PBAN 1-33.

| Injected material (10 pmol) | Pigmented area | Non pigmented area |
|---|---|---|
| None (untreated control) | 93% | 7% |
| Buffer (control) | 85% | 15% |
| PBAN (1-33) $NH_2$ | 96% | 4% |
| PBAN (9-18) COOH | 75% | 25% |

Pigmented and non-pigmented areas were determined by a computerized optical density scanner as described by Altstein et al., (Peptides, submitted, 1994).

What is claimed is:

1. A method for controlling insects comprising applying composition comprising a peptide having the amino acid sequence SEQ. ID. NO. 3, wherein the carboxy-terminal aspartic acid of SEQ ID NO. 3 is the free acid, and an agriculturally acceptable carrier, to agricultural produce in an amount effective to inhibit pheromone production by said insects.

2. The method of claim 1, wherein said insects are of the genus Heliothis.

3. A method for controlling insects comprising applying a composition comprising a peptide having the amino acid sequence of SEQ. ID. NO. 3, wherein the carboxy-terminal aspartic acid of SEQ ID NO. 3 is the free acid, and an agriculturally acceptable carrier, to agricultural produce in an amount effective to inhibit melanization of larvae of said insects.

4. The method of claim 3, wherein said insects are of the genus Spodoptera.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 33 amino acids
      (B) TYPE: amino acid
      (C) STRANDEDNESS: Not Relevant
      (D) TOPOLOGY: linear (ii) MOLECULE TYPE: peptide (ix) FEATURE:
      (A) NAME/KEY: CDS
      (B) LOCATION: 58..1929

(xi) SEQUENCE DESCRIPTION: SEQ ID NO:1:

Leu Ser Asp Asp Met Pro Ala Thr Pro Ala Asp Gln Glu Met Tyr Arg
1            5                   10               15

Gln Asp Pro Glu Gln Ile Asp Ser Arg Thr Lys Tyr Phe Ser Pro Arg
          20                   25               30

Leu (2) INFORMATION FOR SEQ ID NO:2:

(i) SEQUENCE CHARACTERISTICS:
      (A) LENGTH: 6 amino acids
      (B) TYPE: amino acid (C) STRANDEDNESS: Not Relevant
            (D) TOPOLOGY: linear (ii) MOLECULE TYPE: peptide (ix) FEATURE:
            (A) NAME/KEY: CDS
            (B) LOCATION: 1..921

(xi) SEQUENCE DESCRIPTION: SEQ ID NO:2:

Tyr Phe Ser Pro Arg Leu
1               5

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:3:

Pro Ala Asp Gln Glu Met Tyr Arg Gln Asp
1               5                   10

(2) INFORMATION FOR SEQ ID NO:4:

(i) SEQUENCE CHARACTERISTICS:
            (A) LENGTH: 25 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:4:

Pro Ala Asp Gln Glu Met Tyr Arg Gln Asp Pro Glu Gln Ile Asp Ser
1               5                   10                  15

Arg Thr Lys Tyr Phe Ser Pro Arg Leu
            20                  25

(2) INFORMATION FOR SEQ ID NO:5:

(i) SEQUENCE CHARACTERISTICS:
            (A) LENGTH: 21 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:5:

Glu Met Tyr Arg Gln Asp Pro Glu Gln Ile Asp Ser Arg Thr Lys Tyr
1               5                   10                  15

Phe Ser Pro Arg Leu
            20

(2) INFORMATION FOR SEQ ID NO:6:

(i) SEQUENCE CHARACTERISTICS:
            (A) LENGTH: 17 amino acids
            (B) TYPE: amino acid
            (C) STRANDEDNESS: Not Relevant
            (D) TOPOLOGY: linear (ii) MOLECULE TYPE: peptide

```
        (xi) SEQUENCE DESCRIPTION: SEQ ID NO:6:

Gln Asp Pro Glu Gln Ile Asp Ser Arg Thr Lys Tyr Phe Ser Pro Arg
1               5                   10                  15
Leu (2) INFORMATION FOR SEQ ID NO:7:

(i) SEQUENCE CHARACTERISTICS:
          (A) LENGTH: 15 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:7:

Pro Glu Gln Ile Asp Ser Arg Thr Lys Tyr Phe Ser Pro Arg Leu
1               5                   10                  15

(2) INFORMATION FOR SEQ ID NO:8:

(i) SEQUENCE CHARACTERISTICS:
          (A) LENGTH: 8 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:8:

Thr Lys Tyr Phe Ser Pro Arg Leu
1               5

(2) INFORMATION FOR SEQ ID NO:9:

(i) SEQUENCE CHARACTERISTICS:
          (A) LENGTH: 6 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:9:

Tyr Phe Ser Pro Arg Leu
1               5
```